United States Patent [19]

De Stoutz

[11] Patent Number: 5,503,832
[45] Date of Patent: Apr. 2, 1996

[54] METHOD FOR EXTRACTING THE SOLUBLE MATERIAL FROM OIL-BEARING BEANS OR SEEDS

[76] Inventor: Jean-Christian De Stoutz, Château de Larringes, 74500 Evian-les-Bains, France

[21] Appl. No.: 385,135

[22] Filed: Feb. 7, 1995

[30] Foreign Application Priority Data

Feb. 15, 1994 [FR] France .................................. 94 01840

[51] Int. Cl.$^6$ .................................................. A61K 35/78
[52] U.S. Cl. ........................... 424/195.1; 426/44; 426/46; 426/425; 530/378
[58] Field of Search ......................... 424/195.1; 530/378; 426/425, 44, 46

[56] References Cited

U.S. PATENT DOCUMENTS

| | | | |
|---|---|---|---|
| 3,288,614 | 11/1966 | Miles | 426/311 |
| 3,870,801 | 3/1975 | Tombs | 426/92 |
| 4,346,122 | 8/1982 | Orthoefer et al. | 426/656 |
| 4,369,198 | 1/1983 | Uchi et al. | 426/271 |
| 5,270,450 | 12/1993 | Westfall et al. | 530/378 |

FOREIGN PATENT DOCUMENTS 2366798  5/1978  France .

*Primary Examiner*—John W. Rollins
*Attorney, Agent, or Firm*—Young & Thompson

[57] ABSTRACT

Method for extracting the soluble matter from oil-bearing beans or seeds in a continuous operation from unprocessed beans or seeds, without their soaking or removal of their skin, including a comminution of the unprocessed seeds while spraying the same with a liquid, followed by a filtration.

8 Claims, 1 Drawing Sheet

1. Soy "milk" (W.P.S.)
2. Conventional soy milk
3. Cow milk

1. Soy "milk" (W.S.P.)
2. Conventional soy milk
3. Cow milk

1. Soy "milk" (W.P.S.)
2. Conventional soy milk
3. Cow milk

METHOD FOR EXTRACTING THE SOLUBLE MATERIAL FROM OIL-BEARING BEANS OR SEEDS

FIELD OF THE INVENTION

The present invention is concerned with a method for extracting the soluble material from oil-bearing beans or seeds and, more particularly with a method for manufacturing a "milk" or creams based on such oil-bearing seeds.

BACKGROUND OF THE INVENTION

Up to now, soy "milk" was obtained industrially from soy beans which first had their skin removed and then were soaked and steeped in water to which had been added in particular sodium bicarbonate, for a duration of ten to twenty four hours at least, depending on the period of the year and on the temperature.

These operations produce a rehydration of the soy beans, such that the latter can then be crushed, processed into a paste, an then pressed and filtered for extracting the soluble material forming the soy "milk". Then, it is necessary to subject this extract to physical and chemical treatments (in particular with a solvent) for eliminating undesirable aromas, grassy tastes and bacteria. Actually, these undesirable aromas and these bacteria develop in the paste as a result of the prolonged steeping of the soy beans. Furthermore, the soy "milk" obtained must be treated at high temperature, to make sure that it is rid of any germs which may have developed therein.

The currently used methods for obtaining milk or creams from oil-bearing seeds for skin care products or other cosmetic products are similar to the manufacturing process of soy milk described hereabove.

The existing techniques necessitate complicated equipment, in particular for the purification of the products obtained and require the intervention of skilled personnel for carrying out correctly all the operations and for ensuring that the final product is of the quality required.

SUMMARY OF THE INVENTION

The present invention is aimed in particular at producing a milk or cremes from oil-bearing seeds.

The object of the present invention is a method for extracting soluble material from oil-bearing beans or seeds, characterized in that this extraction is carried out in a continuous process, from unprocessed beans or seeds, without soaking them or removing their skin, and in that it includes a comminution of the unprocessed seeds while spraying them with a liquid, followed by a filtration.

The present process for producing a milk or a cream from oil-bearing seeds is particularly interesting since it makes it possible to use the unprocessed beans or seeds, without soaking or steeping, skin removal or transformation into a flour, i.e. as they are obtained after harvesting, without any further operation.

Accordingly and as is described hereafter, it is possible to eliminate the addition of any chemical or of solvent when making the milk or the cream, which also makes it possible to eliminate any operation as was needed previously for retrieving such chemicals and for purifying the product obtained. Furthermore, as prolonged soaking and steeping of the seeds are avoided, any proliferation of germs and bacteria is prevented, so that the milk obtained can be subjected to a thermal treatment at a relatively low temperature, sufficient for ensuring the quality and the conservation of the end product, but much less denaturating for the end product than a high temperature treatment.

DETAILED DESCRIPTION OF THE INVENTION

The present method for producing a milk or a cream of oil-bearing seeds includes the following successive operations:

1. The unprocessed oil-bearing beans or seeds as harvested are finely comminuted in a continuous process (particles lesser than 1 millimetre) while injecting or spraying the same with hot water. The temperature of the sprayed water is generally comprised between 70° and 100° C. and its flow rate is dependent upon the quantity of beans comminuted. This operation of comminution and spraying with water lasts approximately 1 to 3 seconds, preferably 2 seconds.

2. The comminuted material is immediately and continuously filtered by centrifugation so as to separate the solid material from the liquids. This filtration is preferably carried out in a conical centrifugal filter. During this phase of filtration-centrifugation, a layer of comminuted material is plated against the surface of the conical centrifugal filter, thus improving the fineness of the filtrate, and while the liquid portion is recovered by suction, the dry portion or pulp is evacuated continuously by the centrifugal force.

A depression is created at the bottom of the filter by the suction or the pumping of the water which had extracted the soluble material, fats, proteins, mineral salts, vitamins, etc, to produce the soy "milk" or the milk of some other oil-bearing seed. Concomitantly with this depression created at the bottom of the filter, a high pressure is created at the top of the filter, which is caused by the rising motion produced by the centrifugal force, of the pulp which is subsequently expelled from the filter, again by the action of the centrifugal force.

This suction at the bottom of the filter combined with the high pressure at the top of the filter causes automatically a phenomenon of deaeration of the filtrate.

It is during this phase of the manufacturing process which lasts roughly ten seconds (8 to 20 seconds for example) that on the one hand the useful components are extracted from the seeds, and on the other hand, the totality of the insoluble material such as pulp residues, cellulose fibers and the external skin of the seeds as well as the various debris such as gravel, sand, etc, are evacuated.

Thus, the combination of these two first operations, comminution-spraying and filtration-centrifugation lasts only a few seconds, generally from 8 to 20 and preferably from 10 to 15 seconds. Owing to this very short duration of the contact between the seed and water (approximately 12 seconds versus 10 to 24 hours of steeping in the known processes), one can prevent the beans from acquiring an unpleasant taste, resulting from the action of enzymes, in particular of a lipoxygenase, because in such a short time this enzyme does not have the time to react. Also, because of the very short contact time of the seeds with water which is preferably at 80° C., a considerable decrease in the bacterial load is achieved, as well as in the amount of factors which, in the case of food products, are nutritionally undesirable (antitrypsin factors).

3. In a third operation which follows immediately the two first ones and which is also carried out continuously, the filtrate obtained, i.e. the milk, is subjected to a thermal treatment at moderate temperature (pasteurization) to ensure its conservation.

This "moderate temperature", which is in the range from 70° to 100° C. (preferably from 90° C. to 100° C.) used in this thermal treatment is made possible by the low bacterial load of the filtrate, and it makes it possible to reduce notably the denaturation of valuable proteins, ensures a better retention of the vitamins and, accordingly, a final soy "milk" is obtained which has a better nutritional value than that obtained through the usual methods or which is, generally speaking, of a better quality than previously, for example in the case of cosmetic milks.

BRIEF DESCRIPTION OF THE DRAWINGS

The following diagrams illustrate the results of comparative tests carried out on the soy "milk" produced by the present process without pre-soaking (W.P.S.), on a conventional soy "milk" and on cow milk.

ADVANTAGES

Figure 1:
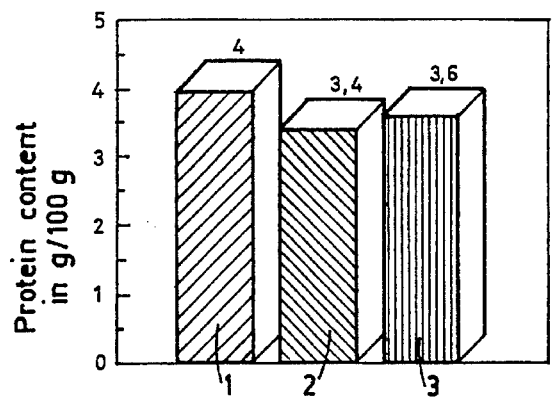
FIG. 1 is a bar graph comparing the protein content in a soy milk prepared according to the present invention, to a conventional soy milk, and to cow milk.
Figure 2:
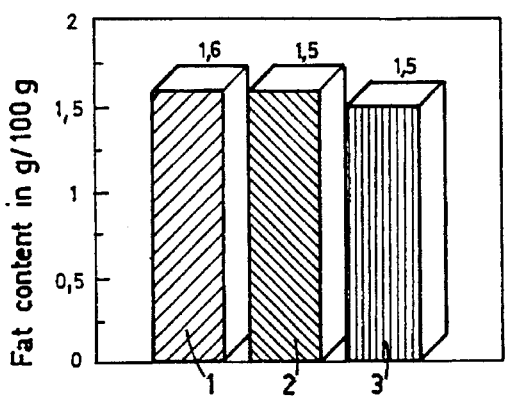
FIG. 2 is a bar graph comparing the content in a soy milk prepared according to the present invention, to a conventional soy milk, and to cow milk.
Figure 3:
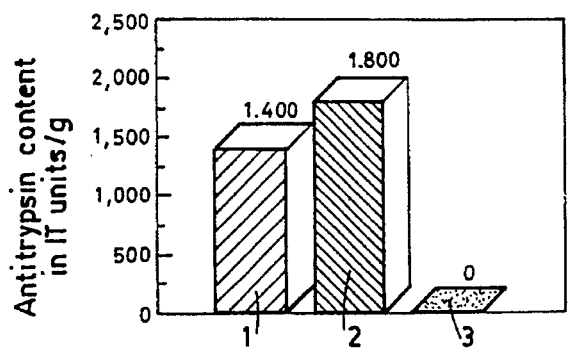
FIG. 3 is a bar graph comparing the antitrypsin content in a soy milk prepared according to the present invention, to a conventional soy milk, and to cow milk.

These diagrams clearly demonstrate that the soy "milk" according to the present W.P.S. process has a higher protein content and a slightly higher fat content than cow milk and a antitrypsin factor content clearly lower than the conventional soy "milk".

In addition to the advantages and to the improved quality of the soy "milk" or of milk from other oil-bearing seeds obtained by the present manufacturing method, this method decreases the energy requirements, owing to the lower temperature at which the thermal treatment takes place and to the absence of chemical treatments.

This method is significantly simpler to implement than the existing methods, since the soaking and seeping are deleted, the seeds are used unprocessed as harvested, all the chemical treatments are eliminated and the process is continuous in all the steps of manufacture.

Accordingly, one can use this manufacturing method in small disseminated production units which can be operated by unskilled staff. These small production units require only a small investment and can be set up directly in areas or villages of poorly developed countries producing soy beans, in which the population suffers from malnutrition.

The above description deals mainly with the production of soy "milk" but clearly, the production method can be used for any extraction of soluble material from oil-bearing beans or seeds, in particular for the manufacture of skin care products and other cosmetic products.

The main novel features of this method are that the beans or the seeds are used as harvested without removal of the skin or soaking and that the duration of the contact between the beans or the seeds and in particular its outer skin is decreased, being less than 30 or 45 seconds and preferably in the order of 10 to 15 seconds.

Clearly, for a proper conservation of the products obtained, when the soy milks and creams are designed for use in skin care, it may be necessary to subject these products to a thermal treatment. This thermal treatment can advantageously be carried out using the Joule effect according to the method described in EP 0.476.311.

I claim:

1. A method for extracting soluble material from soy beans, by carrying out the extraction in a continuous process from unprocessed soy beans without soaking or skin removal, comprising:

comminuting the unprocessed soy beans while spraying them with hot water having a temperature ranging from 70° to 100° C. for a period of less than one minute to obtain comminuted soy beans having a size in the order of 1 mm;

filtering the comminuted soy beans in a centrifugal filter so as to separate solid residues from a filtrate; and recovering said filtrate by suction, and expelling solid residues from the centrifugal filter.

2. A method according to claim 1, wherein the hot water has a temperature ranging from 90° to 100° C.

3. A method according to claim 1, wherein the suction of the filtrate is carried out at a lower part of the centrifugal filter and the expulsion of the debris is carried out at an upper part of the centrifugal filter, said suction and expulsion creating in the centrifugal filter a gradient of pressure causing a deaeration.

4. A method according to claim 1, wherein the period of contact of the hot water with the soy beans is less than 30 seconds.

5. A method according to claim 4, wherein the period of contact with the hot water is in the range of 10 to 15 seconds.

6. A method according to claim 1, further including the step of subjecting the filtrate to a thermal treatment at a temperature less than 120° C.

7. A method according to claim 6, wherein the filtrate is subjected to a thermal treatment at a temperature ranging from 70° to 100° C.

8. A milk from soy beans obtained by the method according to claim 1.

* * * * *